(12) United States Patent
Stoltz et al.

(10) Patent No.: US 7,143,769 B2
(45) Date of Patent: Dec. 5, 2006

(54) CONTROLLING PULSE ENERGY OF AN OPTICAL AMPLIFIER BY CONTROLLING PUMP DIODE CURRENT

(76) Inventors: Richard Stoltz, 2602 Challenger Tech Ct., Suite 240, Orlando, FL (US) 32826; Peter J. Delfyett, 2602 Challenger Tech Ct., Suite 240, Orlando, FL (US) 32826

( * ) Notice: Subject to any disclaimer, the term of this patent is extended or adjusted under 35 U.S.C. 154(b) by 0 days.

(21) Appl. No.: 10/916,367

(22) Filed: Aug. 11, 2004

(65) Prior Publication Data

US 2005/0171518 A1    Aug. 4, 2005

Related U.S. Application Data

(60) Provisional application No. 60/503,578, filed on Sep. 17, 2003, provisional application No. 60/494,275, filed on Aug. 11, 2003.

(51) Int. Cl.
*A61B 19/00* (2006.01)
*A61B 18/18* (2006.01)
*H01S 3/00* (2006.01)

(52) U.S. Cl. ............................ 128/898; 606/10; 606/12; 359/333; 359/345

(58) Field of Classification Search .............. 606/4–12; 607/88, 89; 128/898; 372/43.01, 45.013; 359/333, 342–349
See application file for complete search history.

(56) References Cited

U.S. PATENT DOCUMENTS

| | | | |
|---|---|---|---|
| 3,631,362 A | 12/1971 | Almasi et al. | |
| 3,808,549 A | 4/1974 | Maurer | |
| 3,963,953 A | 6/1976 | Thornton, Jr. | |
| 4,718,418 A | 1/1988 | L'Esperance, Jr. | |
| 4,750,809 A | 6/1988 | Kafka et al. | |
| 4,815,079 A | 3/1989 | Snitzer et al. | |
| 4,824,598 A | 4/1989 | Stokowski | |
| 4,829,529 A | 5/1989 | Kafka | |
| 4,902,127 A | 2/1990 | Byer et al. | |
| 4,913,520 A | 4/1990 | Kafka | |
| 4,972,423 A | 11/1990 | Alfano et al. | |
| 5,162,643 A | 11/1992 | Currie | |
| 5,166,818 A | 11/1992 | Chase et al. | |
| 5,187,759 A | 2/1993 | DiGiovanni et al. | |
| 5,237,576 A | 8/1993 | DiGiovanni et al. | |
| 5,265,107 A | 11/1993 | Delfyett, Jr. | |
| 5,291,501 A | 3/1994 | Hanna | |
| 5,302,835 A | 4/1994 | Bendett et al. | |
| 5,313,262 A | 5/1994 | Leonard | |
| 5,329,398 A | 7/1994 | Lai et al. | |
| 5,400,350 A | 3/1995 | Galvanauskas | |

(Continued)

FOREIGN PATENT DOCUMENTS

JP    2003181661 A    7/2003

(Continued)

OTHER PUBLICATIONS

U.S. Appl. No. 10/916,368, Richard Stoltz, Pulse Energy Adjustment for Changes in Ablation Spot Size, filed Aug. 11, 2004.

(Continued)

*Primary Examiner*—A. Farah
(74) *Attorney, Agent, or Firm*—Carr & Ferrell LLP (57) ABSTRACT

The present invention includes the method of using optically-pumped optical amplifiers to remove material from a body by optical-ablation through time-compressing the amplified pulse and illuminating a portion of the body with the time-compressed optical pulse. The pulse energy of semiconductor optical amplifiers may also be adjusted by controlling the pump diode current.

20 Claims, 2 Drawing Sheets

U.S. PATENT DOCUMENTS

| | | |
|---|---|---|
| 5,414,725 A | 5/1995 | Fermann et al. |
| 5,418,809 A | 5/1995 | August, Jr. et al. |
| 5,430,572 A | 7/1995 | DiGiovanni et al. |
| 5,440,573 A | 8/1995 | Fermann |
| 5,450,427 A | 9/1995 | Fermann et al. |
| 5,479,422 A | 12/1995 | Fermann et al. |
| 5,489,984 A | 2/1996 | Hariharan et al. |
| 5,499,134 A | 3/1996 | Galvanauskas et al. |
| 5,517,043 A | 5/1996 | Ma et al. |
| 5,572,335 A | 11/1996 | Stevens |
| 5,572,358 A | 11/1996 | Gabl et al. |
| 5,585,652 A | 12/1996 | Kamasz et al. |
| 5,585,913 A | 12/1996 | Hariharan et al. |
| 5,592,327 A | 1/1997 | Gabl et al. |
| 5,596,668 A | 1/1997 | DiGiovanni et al. |
| 5,602,677 A | 2/1997 | Tournois |
| 5,617,434 A | 4/1997 | Tamura et al. |
| 5,627,848 A | 5/1997 | Fermann et al. |
| 5,633,750 A | 5/1997 | Nogiwa et al. |
| 5,633,885 A | 5/1997 | Galvanauskas et al. |
| 5,656,186 A | 8/1997 | Mourou et al. |
| 5,663,731 A | 9/1997 | Theodoras, II et al. |
| 5,677,769 A | 10/1997 | Bendett |
| 5,689,519 A | 11/1997 | Fermann et al. |
| 5,696,782 A | 12/1997 | Harter et al. |
| 5,701,319 A | 12/1997 | Fermann |
| 5,703,639 A | 12/1997 | Farrier et al. |
| 5,708,669 A | 1/1998 | DiGiovanni et al. |
| 5,710,424 A | 1/1998 | Thoedoras, II et al. |
| 5,720,894 A | 2/1998 | Neev et al. |
| 5,726,855 A | 3/1998 | Mourou et al. |
| 5,778,016 A | 7/1998 | Sucha et al. |
| 5,818,630 A | 10/1998 | Fermann et al. |
| 5,822,097 A | 10/1998 | Tournois |
| 5,847,863 A | 12/1998 | Galvanauskas et al. |
| 5,862,287 A | 1/1999 | Stock et al. |
| 5,867,304 A | 2/1999 | Galvanauskas et al. |
| 5,875,408 A | 2/1999 | Bendett et al. |
| 5,880,823 A | 3/1999 | Lu |
| 5,880,877 A | 3/1999 | Fermann et al. |
| 5,898,485 A | 4/1999 | Nati, Jr. |
| 5,920,668 A | 7/1999 | Uehara et al. |
| 5,923,686 A | 7/1999 | Fermann et al. |
| 5,936,716 A | 8/1999 | Pinsukanjana et al. |
| 6,014,249 A | 1/2000 | Fermann et al. |
| 6,020,591 A | 2/2000 | Harter et al. |
| 6,034,975 A | 3/2000 | Harter et al. |
| 6,061,373 A | 5/2000 | Brockman et al. |
| 6,072,811 A | 6/2000 | Fermann et al. |
| 6,075,588 A | 6/2000 | Pinsukanjana et al. |
| 6,081,369 A | 6/2000 | Waarts et al. |
| 6,120,857 A | 9/2000 | Balooch et al. |
| 6,130,780 A | 10/2000 | Joannopoulos et al. |
| 6,151,338 A | 11/2000 | Grubb et al. |
| 6,154,310 A | 11/2000 | Galvanauskas et al. |
| 6,156,030 A * | 12/2000 | Neev ............................ 606/10 |
| 6,181,463 B1 | 1/2001 | Galvanauskas et al. |
| 6,198,568 B1 | 3/2001 | Galvanauskas et al. |
| 6,208,458 B1 | 3/2001 | Galvanauskas et al. |
| 6,249,630 B1 | 6/2001 | Stock et al. |
| 6,252,892 B1 | 6/2001 | Jiang et al. |
| 6,256,328 B1 | 7/2001 | Delfyett et al. |
| 6,269,108 B1 | 7/2001 | Tabirian et al. |
| 6,275,512 B1 | 8/2001 | Fermann |
| 6,303,903 B1 | 10/2001 | Liu |
| 6,314,115 B1 | 11/2001 | Delfyett et al. |
| 6,327,074 B1 | 12/2001 | Bass et al. |
| 6,327,282 B1 | 12/2001 | Hammons et al. |
| 6,334,011 B1 | 12/2001 | Galvanauskas et al. |
| 6,335,821 B1 | 1/2002 | Suzuki et al. |
| RE37,585 E | 3/2002 | Mourou et al. |
| 6,355,908 B1 | 3/2002 | Tatah et al. |
| 6,362,454 B1 | 3/2002 | Liu |
| 6,365,869 B1 | 4/2002 | Swain et al. |
| 6,404,944 B1 | 6/2002 | Wa et al. |
| 6,421,169 B1 | 7/2002 | Bonnedal et al. |
| 6,433,303 B1 | 8/2002 | Liu et al. |
| 6,433,305 B1 | 8/2002 | Liu et al. |
| 6,433,760 B1 | 8/2002 | Vaissie et al. |
| 6,501,590 B1 | 12/2002 | Bass et al. |
| 6,522,460 B1 | 2/2003 | Bonnedal et al. |
| 6,525,873 B1 | 2/2003 | Gerrish et al. |
| 6,526,327 B1 | 2/2003 | Kar et al. |
| 6,529,319 B1 | 3/2003 | Youn et al. |
| 6,549,547 B1 | 4/2003 | Galvanauskas et al. |
| 6,567,431 B1 | 5/2003 | Tabirian et al. |
| 6,573,813 B1 | 6/2003 | Joannopoulos et al. |
| 6,574,024 B1 | 6/2003 | Liu |
| 6,576,917 B1 | 6/2003 | Silfvast |
| 6,580,553 B1 | 6/2003 | Kim et al. |
| 6,597,497 B1 | 7/2003 | Wang et al. |
| 6,603,911 B1 | 8/2003 | Fink et al. |
| 6,621,045 B1 | 9/2003 | Liu et al. |
| 6,627,844 B1 | 9/2003 | Liu et al. |
| 6,642,477 B1 | 11/2003 | Patel et al. |
| 6,647,031 B1 | 11/2003 | Delfyett et al. |
| 6,654,161 B1 | 11/2003 | Bass et al. |
| 6,661,816 B1 | 12/2003 | Delfyett et al. |
| 6,671,298 B1 | 12/2003 | Delfyett et al. |
| 6,690,686 B1 | 2/2004 | Delfyett et al. |
| 6,710,288 B1 | 3/2004 | Liu et al. |
| 6,710,293 B1 | 3/2004 | Liu et al. |
| 6,720,519 B1 | 4/2004 | Liu et al. |
| 6,723,991 B1 | 4/2004 | Sucha et al. |
| 6,728,439 B1 | 4/2004 | Weisberg et al. |
| 6,735,229 B1 | 5/2004 | Delfyett et al. |
| 6,738,144 B1 | 5/2004 | Dogariu |
| 6,744,555 B1 | 6/2004 | Galvanauskas et al. |
| 6,749,285 B1 | 6/2004 | Liu et al. |
| 6,774,869 B1 | 8/2004 | Biocca et al. |
| 6,782,207 B1 | 8/2004 | Efimov |
| 6,787,734 B1 | 9/2004 | Liu |
| 6,788,864 B1 | 9/2004 | Ahmad et al. |
| 6,791,060 B1 | 9/2004 | Dunsky et al. |
| 6,801,551 B1 | 10/2004 | Delfyett et al. |
| 6,803,539 B1 | 10/2004 | Liu et al. |
| 6,804,574 B1 | 10/2004 | Liu et al. |
| 6,807,375 B1 | 10/2004 | Dogariu |
| 6,815,638 B1 | 11/2004 | Liu |
| 6,819,694 B1 | 11/2004 | Jiang et al. |
| 6,819,837 B1 | 11/2004 | Li et al. |
| 6,822,251 B1 | 11/2004 | Arenberg et al. |
| 6,829,517 B1 | 12/2004 | Cheng et al. |
| 6,878,900 B1 | 4/2005 | Corkum et al. |
| 6,897,405 B1 | 5/2005 | Cheng et al. |
| 2002/0176676 A1 | 11/2002 | Johnson et al. |
| 2004/0231682 A1 | 11/2004 | Stoltz |
| 2005/0035097 A1 | 2/2005 | Stoltz |
| 2005/0061779 A1 | 3/2005 | Blumenfeld et al. |
| 2005/0065502 A1 | 3/2005 | Stoltz |
| 2005/0074974 A1 | 4/2005 | Stoltz |
| 2005/0077275 A1 | 4/2005 | Stoltz |
| 2005/0127049 A1 | 6/2005 | Woeste et al. |
| 2005/0167405 A1 | 8/2005 | Stoltz et al. |
| 2005/0171516 A1 | 8/2005 | Stoltz et al. |
| 2005/0177143 A1 | 8/2005 | Bullington et al. |
| 2005/0195726 A1 | 9/2005 | Bullington et al. |
| 2006/0064079 A1* | 3/2006 | Stoltz et al. .................. 606/10 |

FOREIGN PATENT DOCUMENTS

| | | | |
|---|---|---|---|
| WO | WO 2004/105100 A2 | 12/2004 | |
| WO | WO 2004/114473 A2 | 12/2004 | |
| WO | WO 2005/018060 A2 | 2/2005 | |

| | | |
|---|---|---|
| WO | WO 2005/018061 A2 | 2/2005 |
| WO | WO 2005/018062 A2 | 2/2005 |
| WO | WO 2005/018063 A2 | 2/2005 |

OTHER PUBLICATIONS

U.S. Appl. No. 10/850,325, Richard Stoltz, Controlling Temperature of an Optical Amplifier by Controlling Pump Diode Current, filed May 19, 2004.

U.S. Appl. No. 11/057,867, Michael Marshall Mielke, Method of Generating an Ultra-Short Pulse Using a High-Frequency Ring Oscillator, filed Feb. 13, 2005.

U.S. Appl. No. 11/057,868, Michael Marshall Mielke, Amplifying of high Energy Laser Pulses, filed Feb. 13, 2005.

U.S. Appl. No. 11/224,867, Peter Delfyett, Laser Ablation Method and Apparatus Having a Feedback Loop and Control Unit, filed Sep. 12, 2005.

U.S. Appl. No. 11/233,634, James F. Brennan, III, Wavelength-Stabilized Pump Diodes for Pumping Gain Media in an Ultrashort Pulsed Laser System, filed Sep. 22, 2005.

U.S. Appl. No. 11/112,256, James F. Brennan, III, Bragg Fibers in Systems for the Generation of High Peak Power Light, filed Apr. 22, 2005.

U.S. Appl. No. 11/229,302, Michael Marshall Mielke, Actively Stabilized Systems for the Generation of Ultrashort Optical Pulses, filed Sep. 15, 2005.

U.S. Appl. No. 10/916,365, Richard Stoltz, Ablative Material Removal with a Preset Removal Rate or Volume or Depth, filed Aug. 11, 2005.

Yeh et al., "Theory of Bragg Fiber", Journal of the Optical Society America, Sep. 1978, pp. 1196, vol. 68, No. 9.

Engeness et al., "Dispersion Tailoring and Compensation by Modal Interations in Omniguide Fibers," Optics Express, May 19, 2003, pp. 1175-1196, vol. 11, No. 10.

Fink et al., "Guiding Optical Light in Air Using an All-Dielectric Structure," Journal of Lightwave Technology, Nov. 1999, pp. 2039-2041, vol. 17, No. 11.

Siegman, "Unstable Optical Resonators", Applied Optics, Feb. 1974, pp. 353-367, vol. 13, No. 2.

Koechner, "Solid State Laser Engineering", Oct. 29, 1999, Sections 5.5, pp. 270-277, 5th Edition, Springer.

Chen et al. "Dispersion-Managed Mode Locking", Journal of the Optical Society of America B, Nov. 1999, pp. 1999-2004, vol. 16, No. 11, Optical Society of America.

Resan et al. "Dispersion-Managed Semiconductor Mode-Locked Ring Laser", Optics Letters, Aug. 1, 2003, pp. 1371-1373, vol. 28, No. 15, Optical Society of America.

Dasgupta, S. et al., "Design of Dispersion-Conpensating Bragg Fiber with an Ultrahigh Figure of Merit," Optics Letters, Aug. 1, 2005, vol. 30, No. 15, Optical Society of America.

Mohammed, W. et al., "Selective Excitation of the TE01 Mode in Hollow-Glass Waveguide Using a Subwavelength Grating," IEEE Photonics Technology Letters, Jul. 2005, vol. 17, No. 7, IEEE.

Delfyett, P et al., "Ultrafast Semiconductor Laser-Diode-Seeded Cr:LiSAF Rengerative Amplifier System", Applied Optics, May 20, 1997, pp. 3375-3380, vol. 36, No. 15, Octoical Society of America.

Levy et al., "Engineering Space-Variant INhomogeneous Media for Polarization Control," Optics Letters, Aug. 1, 2004, pp. 1718-1720, vol. 29, No. 15, Optical Society of America.

Ibanescu et al., "Analysis of Mode Structure in Hollow Dielectric Waveguide Fibers," Physical Review E 67, 2003, The American Physical Society.

* cited by examiner

CONTROLLING PULSE ENERGY OF AN OPTICAL AMPLIFIER BY CONTROLLING PUMP DIODE CURRENT

CROSS-REFERENCE TO RELATED APPLICATIONS

This application claims priority to U.S. Provisional Patent Applications, Ser. No. 60/494,275; entitled "Controlling Pulse Energy Of A Fiber Amplifier By Controlling Pump Diode Current," filed Aug. 11, 2003; and Ser. No. 60/503,578, entitled "Controlling Optically-Pumped Optical Pulse Amplifiers," filed Sep. 17, 2003.

TECHNICAL FIELD OF THE INVENTION

The present invention relates in general to the field of light amplification and more particularly to ablative material removal with an optical pulse.

BACKGROUND OF THE INVENTION

Ablative material removal is especially useful for medical purposes, either in-vivo or on the outside surface (e.g., skin or tooth), as it is essentially non-thermal and generally painless. Ablative removal of material is generally performed with a short optical pulse that is stretched amplified and then compressed. A number of types of laser amplifiers have been used for the amplification.

Laser machining can remove ablatively material by disassociate the surface atoms and melting the material. Laser ablation is efficiently done with a beam of short pulses (generally a pulse-duration of three picoseconds or less). Techniques for generating these ultra-short pulses are described, e.g., in a book entitled "Femtosecond Laser Pulses" (C. Rulliere—editor), published 1998, Springer-Verlag Berlin Heidelberg New York. Generally, large systems, such as Ti:Sapphire, are used for generating ultra-short pulses (USP).

USP phenomenon was first observed in the 1970's, when it was discovered that mode-locking a broad-spectrum laser could produce ultra-short pulses. The minimum pulse duration attainable is limited by the bandwidth of the gain medium, which is inversely proportional to this minimal or Fourier-transform-limited pulse duration. Mode-locked pulses are typically very short and will spread (i.e., undergo temporal dispersion) as they traverse any medium. Subsequent pulse-compression techniques are often used to obtain USP's. Pulse dispersion can occur within the laser cavity so that compression techniques are sometimes added intra-cavity. When high-power pulses are desired, they are intentionally lengthened before amplification to avoid internal component optical damage. This is referred to as "Chirped Pulse Amplification" (CPA). The pulse is subsequently compressed to obtain a high peak power (pulse-energy amplification and pulse-duration compression).

SUMMARY OF THE INVENTION

Ablative material removal using short optical pulse is especially useful for medical purposes and can be done either in-vivo or on the body surface. An optically-pumped optical amplifier can be used for ablation. As ablation is most efficient at about three times the material's ablation threshold, and thus control of pulse energy density is desirable. Pulse energy density can be controlled by controlling pulse energy or by controlling spot size. If the spot size is fixed or otherwise known, this can be achieved by controlling pulse energy; or if the pulse energy is known, by controlling spot size. It is preferred that ablation rate be controllable independent of pulse energy.

A novel control of pulse energy has been developed that is much more convenient than changing the ablation spot size, namely, control pulse energy. It has been found that in optically-pumped optical amplifiers, control of pulse energy of the optical amplifier can be by controlling pump diode current. The pulse energy of semiconductor optical amplifiers may be adjusted by changing the current through the amplifier diodes as either the primary control of pulse energy, or as a fine-tuning to another type of pulse energy control. Further, it is preferred that ablation rate be controllable independent of pulse energy. The use of more than one amplifier in a train mode (pulses from one amplifier being delayed to arrive one or more nanoseconds after those from another amplifier) allows step-wise control of ablation rate independent of pulse energy. At lower desired ablation rates, one or more amplifiers can be shut off (e.g., the optical pumping to the optical amplifier shut off), and there will be fewer pulses per train. Controlling the optical pumping power can be the fine-tuning the ablation pulse energy (e.g., with rep rate control as the primary control), it can also be used alone, in which case the repetition rate control is not necessary.

It has been found that pulse energy of optically-pumped optical amplifiers can be controlled by pump diode current. The pulse energy of semiconductor optical amplifiers can be adjusted by changing the current through the amplifier diodes as either the primary control of pulse energy, or as a fine-tuning to another type of pulse energy control.

Furthermore, the use of more than one amplifier in a train mode (pulses from one amplifier being delayed to arrive one or more nanoseconds after those from another amplifier) allows step-wise control of ablation rate. Thus, at lower desired ablation rates, one or more amplifiers can be shut off (e.g., the optical pumping to the optical amplifier shut off), and there will be fewer pulses per train.

The use of train mode amplifiers provides faster ablation, while providing greater cooling surface area to minimize thermal problems. In addition, one or more of the amplifiers can be shut down, allowing more efficient ablation of a variety of materials with different ablation thresholds, as surfaces are most efficiently ablated at an energy density about three time threshold.

In one embodiment, one or more wavelength-swept-with-time pulses from a semiconductor oscillator-driven pulse generator of between 10 picoseconds and one nanosecond were generated, with the initial pulse amplified by a optical-amplifier, e.g., a erbium-doped fiber amplifier (or EDFA) or a Cr:YAG amplifier and compressed by an "air-path between gratings compressor" (e.g., a Tracey grating compressor is an air-path grating compressor), with the compression creating a sub-picosecond ablation pulse.

Ablative material removal with a very short optical pulse is especially useful for medical purposes and can be done either in-vivo or on the body surface. As some materials ablate much faster than others and material is removed most efficiently at pulse energy densities about three times the materials ablation threshold, the control of the ablation rate is desirable.

Typically, the ablation has a threshold of less than 1 Joule per square centimeter, but occasionally surgical removal of foreign material may require dealing with an ablation threshold of up to about 2 Joules per square centimeter. It was found that control of pulse energy is much more convenient than changing the ablation spot size, and thus control of pulse energy density is desirable. It was further found that in optical amplifiers, this can be done by controlling repetition rate or by controlling the optical pumping power. Thus, the pulse energy of optical amplifiers can be adjusted by changing the current through the amplifier's pump diodes. Further, it is preferred that ablation rate be controllable independent of pulse energy. The use of more than one amplifier in parallel a train mode (pulses from one amplifier being delayed to arrive one or more nanoseconds after those from another amplifier) allows step-wise control of ablation rate independent of pulse energy density. At lower desired ablation rates, one or more amplifiers can be shut down.

Figure 1:
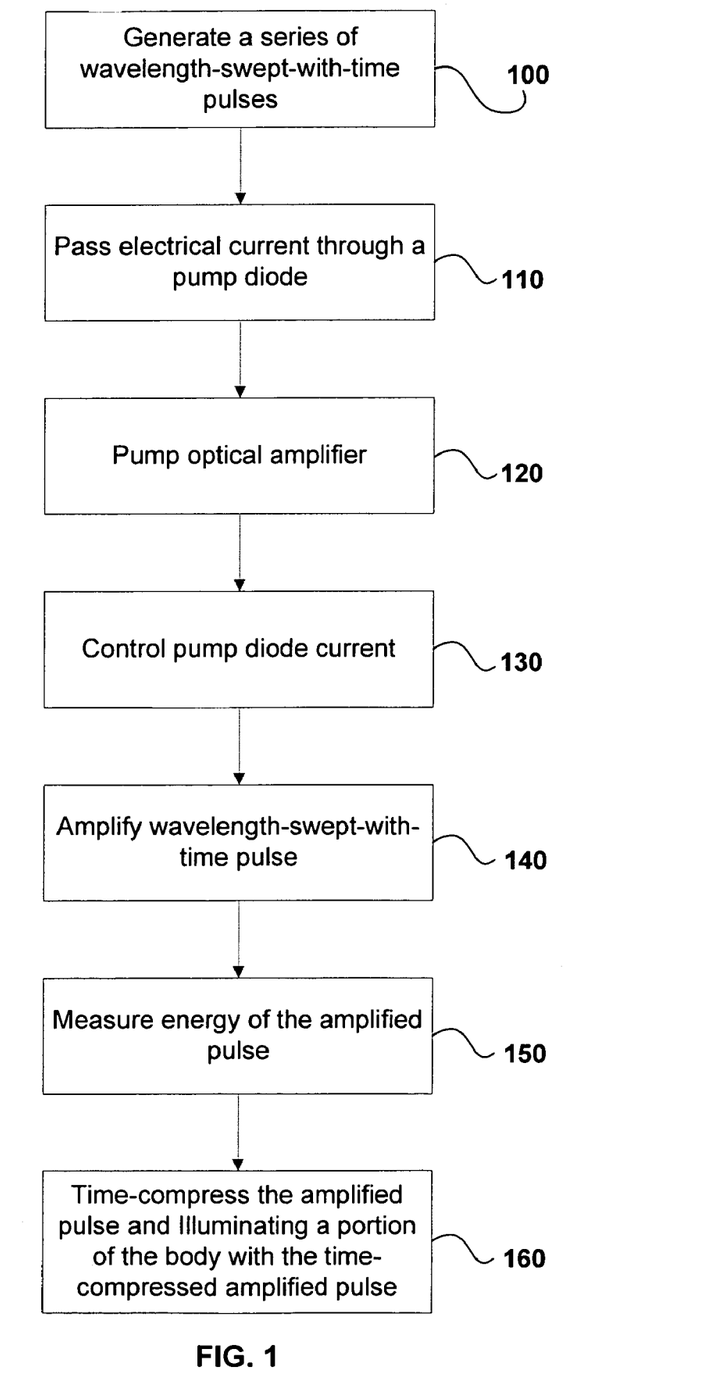
FIG. 1 is a flowchart illustrating the method used in one embodiment of the invention.

As illustrated in FIG. 1, using the present invention, a method of material removal from a body by optical-ablation with controlled pulse energy, includes: Step 100, utilizing an optically-pumped oscillator in the generation of a series of wavelength-swept-with-time pulses; Step 110, passing electrical current through at least one pump diode to generate pumping light; Step 120, optically pumping a optical amplifier with the pumping light; Step 130, controlling pump diode current; Step 140, amplifying the oscillator wavelength-swept-with-time pulse with the optical-amplifier; Step 150, measuring an energy of the amplified pulses; and Step 160, time-compressing the amplified pulse and illuminating a portion of the body with the time-compressed optical pulse, whereby controlling the pump diode current varies the pulse energy of the amplified pulse. When multiple pump diodes are used, the control of pump current can be by turning of the current to one or more pump diodes.

Preferably, the initial generation of a series of wavelength-swept-with-time pulses is at a fixed repetition rate. In some embodiments pulses are selected from the oscillator generated series of wavelength-swept-with-time pulses, and controlling the fraction of pulses selected gives a selected pulse repetition rate that is a fraction of the oscillator repetition rate. In these embodiments, pulse selection is the primary control of pulse energy and controlling of pump diode current is a secondary (fine-tuning) control of pulse energy.

In some embodiments, the oscillator, amplifier and compressor are within a man-portable system, and/or the compression is done in an air-path between gratings compressor. In one example, the compressed optical pulse has a sub-picosecond duration, and the oscillator pulse has a duration between 10 picoseconds and one nanosecond. The ablation can be on an outside surface of the body or done inside of the body. In another example, the pulse energy density applied to the body is between 2.5 and 3.6 times ablation threshold of the body portion being ablated. In some embodiments, more than one amplifier is used in a mode where amplified pulses from one amplifier are delayed to arrive one or more nanoseconds after those from any other amplifier, to allow control of ablation rate independent of pulse energy.

The amplifying and compressing can be done with a optical-amplifier and air-path between gratings compressor combination, e.g., with the amplified pulses between 10 picoseconds and one nanosecond, or the amplifying and compressing can be done with a chirped fiber compressor combination, e.g., with the initial pulses between 1 and 20 nanoseconds. The optical amplifier preferably is an erbium-doped fiber amplifier or a Cr:YAG amplifier, and the air-path between gratings compressor preferably is a Tracey grating compressor.

Preferably, more than one optical amplifiers are used in parallel, or more than one semiconductor optical amplifiers are used in parallel. More than one optical amplifiers may be used with one compressor. High ablative pulse repetition rates are preferred and the total pulses per second (the total system repetition rate) from the one or more parallel optical amplifiers is preferably greater than 0.6 million. In some embodiments the system may be man-portable system comprising a wheeled cart or backpack.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Ablative material removal using short optical pulse can be done either in-vivo or on the body surface. An optically-pumped optical amplifier can be used for ablation. If the spot size is fixed or otherwise known, pulse energy density can be controlled by controlling pulse energy; or if the pulse energy is known, by controlling spot size. A novel control of pulse energy was developed that is much more convenient than changing the ablation spot size, to control pulse energy. It was found that in optical amplifiers, control of pulse energy of an optical amplifier can be by controlling pump diode current. The pulse energy of semiconductor optical amplifiers can be adjusted by changing the current through the amplifier diodes as either the primary control of pulse energy, or as a fine-tuning to another type of pulse energy control.

It was also found that the combination of optical-amplifier/a small pulse-compressor enables practical, and significant size reduction, which in turn enables the system to be portable as a wheeled cart or a backpack. As used herein, the term "portable" generally means capable of being moved reasonably easily by one person, e.g., as wheeling a wheeled cart from room to room or possibly even being carried in a backpack.

Figure 2:
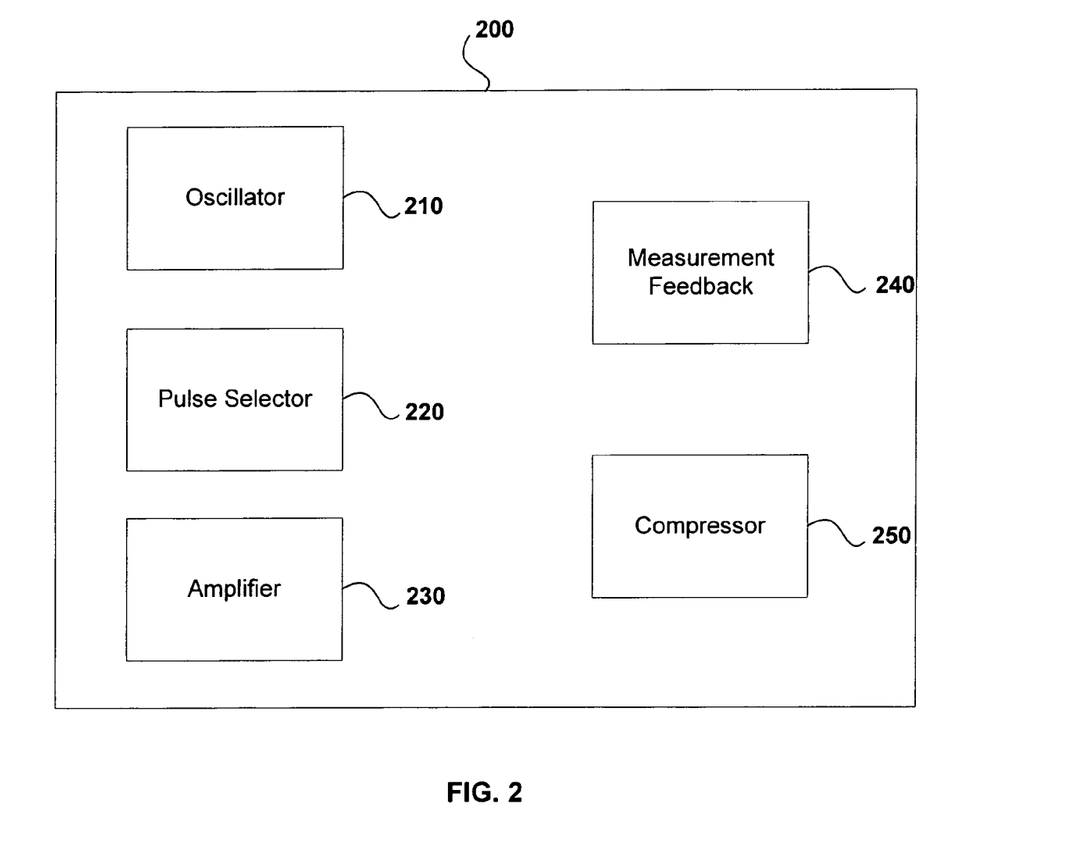
FIG. 2 is a block diagram of a system implementing one embodiment of the invention.

As illustrated by the embodiment in FIG. 2, a system 200 for material removal from a body by optical-ablation with controlled pulse energy, may comprise an optical oscillator 210 to generate a series of wavelength-swept-with-time pulses; a pulse selector 220 for selecting pulses from the series of wavelength-swept-with-time pulses for controlling ablation pulse energy; an optical amplifier 230 for amplifying the wavelength-swept-with-time pulses to produce amplified pulses; a measurement feedback 240 for measuring an energy of the amplified pulses; and a compressor 250 for time-compressing the amplified pulses.

In one embodiment, one or more sub-picosecond pulses of between 10 picoseconds and one nanosecond, followed by pulse selection, with the selected pulses amplified by a optical-amplifier were generated (e.g., a erbium-doped fiber amplifier or EDFA or a Cr:YAG amplifier) and compressed by an air-path between gratings compressor (e.g., a Tracey grating compressor), with the compression creating a sub-picosecond ablation pulse. Generally, a semiconductor oscillator may be used to generate pulses and in some embodiments a semiconductor optical amplifier (SOA) preamplifier is used to amplify the selected pulses before introduction into the optical amplifier.

While the compressors can be run with inputs from more than one amplifier, reflections from other of the parallel amplifiers can cause a loss of efficiency, and thus should be minimized. The loss is especially important if one or more than one amplifiers is amplifying signals at the same time, as is the case with the SOAs. Thus, each of the parallel SOAs preferably has its own compressor and while the amplified pulses may be put into a single optical after the compressors, reflections from the joining (e.g., in a star connector) are reduced greatly before getting back to the amplifier. With the optical amplifiers, however, a nanosecond spacing of sub-nanosecond pulses minimizes amplifying of multiple signals at the same time, and a single compressor may preferably be used.

Fiber amplifiers have a storage lifetime of about 100 to 300 microseconds, and for ablations purposes, fiber amplifiers have generally heretofore been operated with a time between pulses of equal to or greater than the storage lifetime, and thus are generally run a rep rate of less than 3–10 kHz. Fiber amplifiers are available with average power of 30 W or more.

A moderate-power 5 W average power optical amplifiers have been operated to give pulses of 500 microJoules or more, as energy densities above the ablation threshold are needed for non-thermal ablation, and increasing the energy in such a system, increases the ablation rate in either depth or allows larger areas of ablation or both. However, the optical amplifier may be run with a time between pulses of a fraction (e.g., one-half or less) of the storage lifetime and used to generate a smaller ablation spot. In one example, the spot is less than about 50 microns in diameter. In another example, a scan of a smaller spot to get a larger effective ablation area is performed.

Also, it may be preferable in some applications to use parallel optical amplifiers to generate a train of pulses to increase the ablation rate by further increasing the effective repetition rate (while avoiding thermal problems and allowing control of ablation rate by the use of a lesser number of operating optical amplifiers). An SOA preamplifier is used to amplify the initial pulse before splitting to drive multiple parallel optical amplifiers and another SOA before the introduction of the signal into each optical amplifier (which allows rapid shutting down of individual optical amplifiers). Further, the system operates with pulses at about three times the ablation threshold for greater ablation efficiency.

The system can be run either with dynamic feedback from measurement of pulse energy with a control point being varied for materials of different ablation thresholds. In another embodiment the system can be run either with an open-loop. The open-loop control could be a selector switch where the selector switch is used to directly or indirectly select a pump diode current and current is controlled to that level, or where a selector switch selects an optical-pumping-power level and the system controls optical-pumping power to that level, but could also be a high/low switch that shuts off current to one of two pump diodes or selects one of two preset pump diode currents. A multi-position selector switch could indicate classes of materials and setting the switch to one of those classes results in the selection of pump diode current. When multiple pump diodes are used for an optical amplifier, the control of pump current can be by turning of the current to one or more pump diodes. Some embodiments include using an ablation spot-size sensor to measure the ablation spot size and dynamically adjusting either the fraction of pulses selected or the pump diode current for changes in the ablation spot size.

The use of a 1 nanosecond pulse with an optical amplifier and air optical-compressor (e.g., a Tracey grating compressor) typically gives compression with ~40% losses. At less than 1 nanosecond, the losses in a Tracey grating compressor are generally lower. If the other-than-compression losses are 10%, 2 nanoJoules are needed from the amplifier to get 1 nanoJoule on the target. For safety purposes, e.g., a 1550 nm light is used. The use of greater than 1 nanosecond pulses in an air optical-compressor presents two problems; the difference in path length for the extremes of long and short wavelengths needs to be more 30 cm and, thus, the compressor is large and expensive, and the losses increase with a greater degree of compression.

Preferably, a semiconductor generated initial pulse is used, e.g., using a SOA preamplifier to amplify the initial pulse before splitting to drive multiple amplifiers. The preferred scan ablates a smaller spot to get a larger effective ablation area, and in many cases the scanned spot is smaller than the above optical-amplifier case. Alternatively, parallel amplifiers may be used to generate a train of pulses to increase the ablation rate by further increasing the total-effective repetition rate (while avoiding thermal problems and allowing control of ablation rate by the use of a lesser number of operating amplifiers).

Ablative material removal is especially useful for medical purposes either in-vivo and/or on the body surface. One embodiment of the present invention has an ablation threshold of less than 1 Joule per square centimeter, however other embodiments may have an ablation threshold of up to about 2 Joules per square centimeter.

The claimed invention may use of more than one amplifier in parallel train mode (pulses from one amplifier being delayed to arrive one or more nanoseconds after those from another amplifier). At lower desired powers, one or more amplifiers can be shut off (e.g., the optical pumping to an optical amplifier), resulting in fewer pulses per train. Thus, with 20 amplifiers there would be a maximum of 20 pulses in a train, but most uses might use only three or four amplifiers and three or four pulses per train.

While CW operation might normally be used for operating amplifiers, amplifiers might be run for e.g., one second and then turned off and a dormant amplifier turned on to spread the heat load. In one embodiment the input optical signal power, optical pumping power of optical amplifiers, timing of input pulses, length of input pulses, and timing between start of optical pumping and start of optical signals to control pulse power, and average degree of energy storage in optical amplifier can be controlled.

In one embodiment multiple fiber amplifiers can be used. Many fiber amplifiers have a maximum power of 4 MW, and thus a 10-microJoule-ablation pulse could be as short as 2 picoseconds. For example, a 10 picosecond, 10 microJoule pulse, at 500 kHz (or 50 microJoule with 100 kHz), and, if heating becomes a problem, operating in a train mode and switching fiber amplifiers. Thus, it is possible to rotate the running of ten fiber amplifiers such that only five were operating at any one time (e.g., each on for $\frac{1}{10}^{th}$ of a second and off for $\frac{1}{10}^{th}$ of a second). Again, the system may use ten fiber amplifiers with time spaced inputs, e.g., by 1 nanosecond, to give a train of one to 10 pulses. With 5 W amplifiers operating at 100 kHz (and e.g., 50 microJoules) this could step between 100 kHz and 1 MHz. With 50% post-amplifier optical efficiency and 50 microJoules, to get 6 J/sq. cm on the target, the spot size would be about 20 microns.

Another embodiment has 20 amplifiers with time spaced inputs, e.g., by 1 ns, to give a train of one to 20 pulses. With 5 W amplifiers operating at 50 kHz (and e.g., 100 microJoules) this could step between 50 kHz and 1 MHz. With 50% post-amplifier optical efficiency and 100 microJoules, to get 6 J/sq. cm on the target, the spot size would be about 33 microns. The amplified pulse might be 50 to 100 picoseconds long. Yet another embodiment may have 15 optical amplifiers could step between 50 kHz and 750 kHz.

With 5 W amplifiers operating at 20 kHz (and e.g., 250 microJoules) and 10 optical amplifiers this could step between 20 kHz and 200 kHz. With 50% post-amplifier optical efficiency and 250 microJoules, to get 6 J/sq. cm on the target, the spot size would be about 50 microns. The amplified pulse might be 100 to 250 picoseconds long. A similar system with 30 optical amplifiers could step between 20 kHz and 600 kHz. Generally, it is the pulse generator that controls the input repetition rate of the optical amplifiers.

Another alternative is generating a sub-picosecond pulse and time stretching that pulse within semiconductor pulse generator to give the initial wavelength-swept-with-time initial pulse. Yet another alternate is to measure light leakage from the delivery fiber to get a feedback proportional to pulse power and/or energy for control purposes. Measurement of spot size, e.g., with a video camera, is useful, and can be done with a stationary spot, but is preferably done with a linear scan.

The camera (even when used externally) is preferably of the "in-vivo" type using (see "Camera Containing Medical Tool" U.S. Provisional Patent Application, Ser. No. 60/472,071 filed May 20, 2003; which is incorporated by reference herein) using an optical fiber in a probe to convey an image back to, e.g., a vidicon-containing remote camera body. This is especially convenient with a handheld beam-emitting probe.

Smaller ablation areas may be scanned by moving the beam without moving the probe. Large areas may be scanned by moving the beam over a first area, and then stepping the probe to second portion of the large area and then scanning the beam over the second area, and so on. The scanning may be by beam deflecting mirrors mounted on piezoelectric actuators (see "Scanned Small Spot Ablation With A High-Rep-Rate" U.S. Provisional Patent Application, Ser. No. 60/471,972, filed May 20, 2003; which is incorporated by reference herein). Preferably, the system actuators scan over a larger region but with the ablation beam only enabled to ablate portions with defined color and/or area. A combination of time, area and/or color, can be preset, e.g., to allow evaluation after a prescribed time.

Information of such a system and other information on ablation systems are given in co-pending provisional applications listed in the following paragraphs (which are also at least partially co-owned by, or exclusively licensed to, the owners hereof) and are hereby incorporated by reference herein (provisional applications listed by docket number, title and provisional number):

Docket number ABI-1 "Laser Machining" U.S. Provisional Patent Application, Ser. No. 60/471,922; ABI-4 "Camera Containing Medical Tool" U.S. Provisional Patent Application, Ser. No. 60/472,071; "Scanned Small Spot Ablation With A High-Rep-Rate" U.S. Provisional Patent Application, Ser. No. 60/471,972; and "Stretched Optical Pulse Amplification and Compression", U.S. Provisional Patent Application, Ser. No. 60/471,971, were filed May 20, 2003;

"Controlling Repetition Rate Of Fiber Amplifier"—U.S. Provisional Patent Application, Ser. No. 60/494,102; "Pulse Energy Adjustment For Changes In Ablation Spot Size"—U.S. Provisional Patent Application, Ser. No. 60/494,274; "Ablative Material Removal With A Preset Removal Rate or Volume or Depth" U.S. Provisional Patent Application, Ser. No. 60/494,273; "Fiber Amplifier With A Time Between Pulses Of A Fraction Of The Storage Lifetime" U.S. Provisional Patent Application, Ser. No. 60/494,321; "Man-Portable Optical Ablation System" U.S. Provisional Patent Application, Ser. No. 60/494,321; "Controlling Temperature Of A Fiber Amplifier By Controlling Pump Diode Current" U.S. Provisional Patent Application, Ser. No. 60/494,322; "Altering The Emission Of An Ablation Beam for Safety or Control" U.S. Provisional Patent Application, Ser. No. 60/494,267; "Enabling Or Blocking The Emission Of An Ablation Beam Based On Color Of Target Area" U.S. Provisional Patent Application, Ser. No. 60/494,172; "Remotely-Controlled Ablation of Surfaces" U.S. Provisional Patent Application, Ser. No. 60/494,276 and "Ablation Of A Custom Shaped Area" U.S. Provisional Patent Application, Ser. No. 60/494,180; were filed Aug. 11, 2003 and "High-Power-Optical-Amplifier Using A Number Of Spaced, Thin Slabs" U.S. Provisional Patent Application, Ser. No. 60/497,404 was filed Aug. 22, 2003;

Co-owned "Spiral-Laser On-A-Disc", U.S. Provisional Patent Application, Ser. No. 60/502,879; and partially co-owned "Laser Beam Propagation in Air", U.S. Provisional Patent Application, Ser. No. 60/502,886 were filed on Sep. 12, 2003; and "Active Optical Compressor" U.S. Provisional Patent Application, Ser. No. 60/503,659, filed Sep. 17, 2003;

"High Power SuperMode Laser Amplifier" U.S. Provisional Patent Application, Ser. No. 60/505,968 was filed Sep. 25, 2003, "Semiconductor Manufacturing Using Optical Ablation" U.S. Provisional Patent Application, Ser. No. 60/508,136 was filed Oct. 2, 2003, "Composite Cutting With Optical Ablation Technique" U.S. Provisional Patent Application, Ser. No. 60/510,855 was filed Oct. 14, 2003 and "Material Composition Analysis Using Optical Ablation", U.S. Provisional Patent Application, Ser. No. 60/512,807 was filed Oct. 20, 2003;

"Quasi-Continuous Current in Optical Pulse Amplifier Systems" U.S. Provisional Patent Application, Ser. No. 60/529,425 and "Optical Pulse Stretching and Compressing" U.S. Provisional Patent Application, Ser. No. 60/529,443, were both filed Dec. 12, 2003;

"Start-up Timing for Optical Ablation System" U.S. Provisional Patent Application, Ser. No. 60/539,026; "High-Frequency Ring Oscillator", Ser. No. 60/539,024; and "Amplifying of High Energy Laser Pulses", U.S. Provisional Patent Application, Ser. No. 60/539,025; were filed Jan. 23, 2004;

"Semiconductor-Type Processing for Solid-State Lasers", U.S. Provisional Patent Application, Ser. No. 60/543,086, was filed Feb. 9, 2004; and "Pulse Streaming of Optically-Pumped Amplifiers", U.S. Provisional Patent Application, Ser. No. 60/546,065, was filed Feb. 18, 2004. "Pumping of Optically-Pumped Amplifiers", U.S. Provisional Patent Application, Ser. No. 60/548,216 filed Feb. 27, 2004.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

What is claimed is:

1. A method of surgical material removal from a body by optical-ablation with controlled pulse energy, comprising the steps of:
   utilizing an optical oscillator in the generation of a series of wavelength-swept-with-time pulses;
   passing electrical current through at least one pump diode to generate pumping light;
   optically pumping an optical amplifier using the pumping light;
   amplifying the wavelength-swept-with-time pulses using the optical amplifier to produce amplified pulses;
   measuring an energy of the amplified pulses;
   controlling pump diode current in order to vary the pulse energy of amplified pulses;
   time-compressing the amplified pulses using a compressor to produce time-compressed amplified pulses;
   illuminating a portion of the body with the time-compressed amplified pulses; and
   using more than one optical amplifiers in a mode in which amplified pulses from a first of the optical amplifiers are delayed such that they arrive one or more nanoseconds after amplified pulses from a second of the optical amplifiers, to enable control of ablation rate independent of pulse energy.

2. The method of claim 1, wherein the optical oscillator, optical amplifier and compressor are within a man-portable system.

3. The method of claim 1, wherein the compressor includes an air-path between gratings compressor.

4. The method of claim 1, wherein the time-compressed amplified pulses have a sub-picosecond duration.

5. The method of claim 1, wherein a member of the wavelength-swept-with-time pulses have a duration between 10 picoseconds and one nanosecond.

6. The method of claim 1, wherein the ablation is from an outside surface of the body.

7. The method of claim 1, wherein the ablation is done inside of the body.

8. The method of claim 1, wherein the optical amplifier is a fiber amplifier.

9. The method of claim 1, wherein the amplified pulses applied to the portion of the body have a pulse energy between 2.5 and 3.6 times an ablation threshold of the portion of the body.

10. The method of claim 1, wherein the generation of a series of wavelength-swept-with-time pulses is at a fixed repetition rate.

11. A method of surgical material removal from a body by optical-ablation with controlled pulse energy, comprising the steps of:
    utilizing an optical oscillator in the generation of a series of wavelength-swept-with-time pulses at a fixed repetition rate;
    passing electrical current through or least one pump diode to generate pumping light;
    optically pumping an optical amplifier using the pumping light;
    amplifying the wavelength-swept-with-time pulses using the optical amplifier to produce amplified pulses;
    measuring an energy of the amplified pulses;
    controlling pump diode current in order to vary the pulse energy of amplified pulses;
    time-compressing the amplified pulses using a compressor to produce time-compressed amplified pulses;
    illuminating a portion of the body with the time-compressed amplified pulses; and
    selecting pulses from the series of wavelength-swept-with-time pulses, pulse selection being configured to be controllably varied to give a selected pulse repetition rate that is a fraction of the fixed repetition rate as a first control of ablation rate and controlling pump diode current as a second control of ablation rate, whereby ablation rate is controllable independent of pulse energy.

12. A method of material removal by optical-ablation with controlled pulse energy, comprising the steps of:
    utilizing an optical oscillator in the generation of a wavelength-swept-with-time pulse;
    passing electrical current through at least one pump diode to generate pumping light;
    optically pumping an optical amplifier, using the pumping light;
    controlling pump diode current;
    amplifying the wavelength-swept-with-time pulse using the optical amplifier to generate an amplified pulse;
    time-compressing the amplified pulse to generate a time-compressed amplified pulse;
    illuminating a portion of the body with the time-compressed amplified pulse, whereby controlling the pump diode current controls the pulse energy of the amplified pulse; and
    delivering the amplified pulse to a target in a manner such that an ablation rate of the material is independent of the pulse energy of the amplified pulse.

13. The method of claim 12, wherein a multi-position selector switch is used to select an optical-pumping-power level and the pump diode current is controlled to control optical-pumping power to that level.

14. The method of claim 12, wherein a selector switch is used to select a pump diode current level and the pump diode current is controlled to that level.

15. The method of claim 12, wherein the optical amplifier is a fiber amplifier.

16. The method of claim 12, wherein an ablation rate is responsive to a first control comprising pulse selection and to a second control comprising varying the amplification of the wavelength-swept-with-time pulses by adjusting a pump diode current, whereby the ablation rate is controllable independent of pulse energy.

17. A system for material removal from a body by optical-ablation with controlled pulse energy, comprising:
    an optical oscillator to generate a series of wavelength-swept-with-time pulses;
    a pulse selector configured for selecting pulses from the series of wavelength-swept-with-time pulses for controlling ablation rate independent of the pulse energy;
    an optical amplifier configured for amplifying the wavelength-swept-with-time pulses to produce amplified pulses;
    a measurement feedback configured for measuring an energy of the amplified pulses and controlling the pulse selector; and a compressor configured for time-compressing the amplified pulses.

18. The system of claim 17, wherein the ablation rate is responsive to a first control comprising the pulse selector and to a second control comprising the optical amplifier wherein amplification of the wavelength-swept-with-time pulses is variable using a pump diode current, whereby ablation rate is controllable independent of pulse energy.

19. The system of claim 17, wherein the measurement feedback is used to control the pump diode current.

20. The system of claim 17, wherein the pulse selector selects a fraction of a total number of the wavelength-swept-with-time pulses, the fraction being responsive to the measurement feedback.

* * * * *